United States Patent
Koseoglu et al.

(10) Patent No.: US 11,603,341 B2
(45) Date of Patent: Mar. 14, 2023

(54) METHODS FOR GAS PHASE OXIDATIVE DESULPHURIZATION OF HYDROCARBONS USING CUZNAL CATALYSTS PROMOTED WITH GROUP VIB METALS

(71) Applicants: SAUDI ARABIAN OIL COMPANY, Dhahran (SA); BORESKOV INSTITUTE OF CATALYSIS, Novosibirsk (RU)

(72) Inventors: Omer Refa Koseoglu, Dhahran (SA); Yaming Luisa Jin, Dhahran (SA); Zinfer Ismagilov, Novosibirsk (RU); Svetlana Letizia Yashnik, Novosibirsk (RU); Anton Salnikov, Novosibirsk (RU); Mikhail Kerzhentsev, Novosibirsk (RU); Valentin Parmon, Novosibirsk (RU)

(73) Assignees: SAUDI ARABIAN OIL COMPANY, Dhahran (SA); BORESKOV INSTITUTE OF CATALYSIS, Novosibirsk (RU)

( * ) Notice: Subject to any disclaimer, the term of this patent is extended or adjusted under 35 U.S.C. 154(b) by 158 days.

(21) Appl. No.: 17/140,667

(22) Filed: Jan. 4, 2021

(65) Prior Publication Data
US 2021/0230084 A1    Jul. 29, 2021

Related U.S. Application Data

(62) Division of application No. 14/987,141, filed on Jan. 4, 2016, now Pat. No. 10,882,801.

(51) Int. Cl.
*C07C 7/148* (2006.01)
*B01J 23/887* (2006.01)
(Continued)

(52) U.S. Cl.
CPC ............ *C07C 7/1485* (2013.01); *B01D 53/48* (2013.01); *B01D 53/8606* (2013.01);
(Continued)

(58) Field of Classification Search
CPC .................. B01J 23/885; B01J 23/8873; B01J 37/0201; B01J 37/031; B01J 37/08
See application file for complete search history.

(56) References Cited

U.S. PATENT DOCUMENTS

| 4,085,065 A | 4/1978 | White et al. |
| 6,693,057 B1 | 2/2004 | Cai et al. |

(Continued)

FOREIGN PATENT DOCUMENTS

| CN | 1090315 A | 8/1994 |
| CN | 103028365 A | 4/2013 |

(Continued)

OTHER PUBLICATIONS

Lu, Yong et al. "Aerobic oxidative desulfurization: A promising approach for sulfur removal from fuels." ChemSusChem: Chemistry & Sustainability Energy & Materials 1.4 (2008): 302-306.

(Continued)

*Primary Examiner* — Jun Li
(74) *Attorney, Agent, or Firm* — Leason Ellis LLP

(57) ABSTRACT

A catalytic composition is disclosed, which exhibits an X-ray amorphous oxide with a spinel formula, and crystals of ZnO, CuO, and at least one Group VIB metal oxide, and preferably, at least one acidic oxide of B, P. or Si, as well. The composition is useful in oxidative processes for removing sulfur from gaseous hydrocarbons.

14 Claims, 5 Drawing Sheets

ODS reactivity comparison for Mo,B-modified CuZnAl catalyst samples: A- Total sulfur removal in the liquid phase, B- Ratio of total sulfur removal to fuel oxidation

(51) Int. Cl.

| | | |
|---|---|---|
| *B01J 37/08* | (2006.01) | |
| *B01J 35/02* | (2006.01) | |
| *B01J 23/885* | (2006.01) | |
| *B01J 23/00* | (2006.01) | |
| *B01J 35/00* | (2006.01) | |
| *B01D 53/48* | (2006.01) | |
| *B01D 53/86* | (2006.01) | |
| *C10G 27/04* | (2006.01) | |
| *B01J 23/80* | (2006.01) | |
| *B01J 35/08* | (2006.01) | |
| *B01J 35/10* | (2006.01) | |
| *B01J 37/02* | (2006.01) | |
| *B01J 37/03* | (2006.01) | |

(52) U.S. Cl.
CPC ............ *B01J 23/005* (2013.01); *B01J 23/80* (2013.01); *B01J 23/885* (2013.01); *B01J 23/8873* (2013.01); *B01J 35/002* (2013.01); *B01J 35/0006* (2013.01); *B01J 35/023* (2013.01); *B01J 35/026* (2013.01); *B01J 35/08* (2013.01); *B01J 35/1014* (2013.01); *B01J 35/1038* (2013.01); *B01J 35/1042* (2013.01); *B01J 35/1061* (2013.01); *B01J 37/0201* (2013.01); *B01J 37/0236* (2013.01); *B01J 37/031* (2013.01); *B01J 37/08* (2013.01); *C07C 7/14808* (2013.01); *C10G 27/04* (2013.01); *B01D 2251/102* (2013.01); *B01D 2255/209* (2013.01); *B01D 2255/2092* (2013.01); *B01D 2255/20761* (2013.01); *B01D 2255/20769* (2013.01); *B01D 2255/20792* (2013.01); *B01D 2255/9202* (2013.01); *B01D 2255/9205* (2013.01); *B01D 2255/9207* (2013.01); *B01D 2256/24* (2013.01); *B01D 2257/306* (2013.01); *C10G 2300/202* (2013.01)

(56) References Cited

U.S. PATENT DOCUMENTS

| | | | |
|---|---|---|---|
| 7,427,581 B2* | 9/2008 | Khare | C10G 25/003 |
| | | | 502/343 |
| 7,749,376 B2 | 7/2010 | Turbevillle et al. | |
| 2006/0035784 A1 | 2/2006 | Wessel et al. | |
| 2007/0034552 A1 | 2/2007 | Tubeville | |
| 2013/0026072 A1 | 1/2013 | Bourane | |
| 2014/0135210 A1* | 5/2014 | Budiman | C01B 3/326 |
| | | | 502/343 |
| 2014/0197074 A1* | 7/2014 | Bourane | B01J 35/1014 |
| | | | 422/187 |

FOREIGN PATENT DOCUMENTS

| | | |
|---|---|---|
| CN | 104136116 A | 11/2014 |
| CN | 104321140 A | 1/2015 |
| CN | 104560250 A | 4/2015 |
| CN | 104437518 B | 3/2017 |
| GB | 1575334 A | 9/1980 |
| JP | 2009-504878 A | 2/2009 |
| JP | 2014-524836 A | 11/2014 |
| KR | 10-2015-0105905 A | 9/2015 |
| WO | 2014/109777 A1 | 7/2014 |

OTHER PUBLICATIONS

Cao, Lida, et al. "Hydrotalcite-like compounds derived CuZnAl oxide catalysts for aerobic oxidative removal of gasoline-range organosulfur compounds." Energy & fuels 23.2 (2009): 624-630.

* cited by examiner

ODS reactivity comparison for Mo,B-modified CuZnAl catalyst samples: A- Total sulfur removal in the liquid phase, B- Ratio of total sulfur removal to fuel oxidation

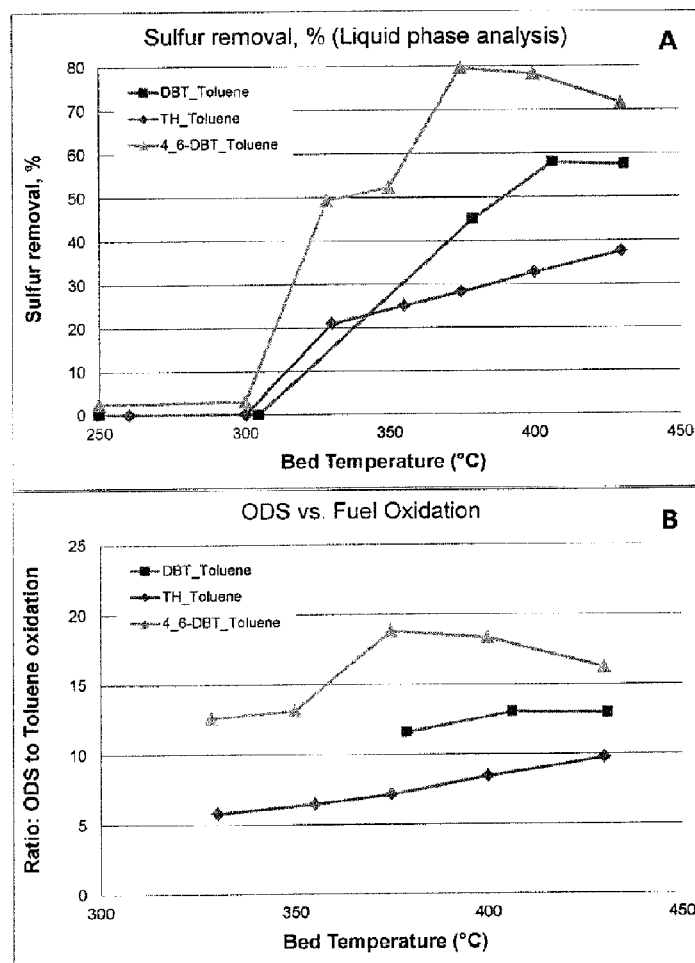
Impact of organosulfur types on ODS reactivity of catalyst V649, A- Total sulfur removal in the liquid phase, B- Ratio of total sulfur removal to fuel oxidation TPR profiles of the Mo,B-modified CuZnAl systems Powder X-ray diffraction patterns of the dried base CuZnAl catalyst, V628

Powder X-ray diffraction patterns of the MoB-modified CuZnAl catalyst, V649

METHODS FOR GAS PHASE OXIDATIVE DESULPHURIZATION OF HYDROCARBONS USING CUZNAL CATALYSTS PROMOTED WITH GROUP VIB METALS

CROSS REFERENCE TO RELATED APPLICATION

This application is a Divisional of prior filed U.S. application Ser. No. 14/987,141, filed Jan. 4, 2016, which is incorporated in its entirety by reference herein, and made a part of this application.

FIELD OF THE INVENTION

This invention relates to Cu/Zn/Al catalysts which are promoted with at least one oxide of a Group VIB metal, such as Mo or W. The resulting catalysts are effective in gas phase, oxidative desulphurization of sulfur containing hydrocarbons, especially gaseous hydrocarbons. In preferred embodiments, the catalysts contain a second promoter, which is an acid forming oxide of B, Si, or P.

BACKGROUND OF THE INVENTION

Gas phase oxidation of sulfur containing hydrocarbons, to remove the sulfur, is a well known process. Examples of such processes are shown in, e.g., U.S. 20130199968, U.S. 20130028822, and U.S. 20130026072, all of which are incorporated by reference herein. U.S. 20130026072, e.g., describes a process for making catalysts which are useful in oxidative desulphurization ('072" hereafter).

The '072 disclosure teaches that cerium can be promoted in Cu/Zn/Al containing catalysts, which are useful in ODS processes. The catalysts are described as amorphous oxides, with a spinel phase and highly dispersed crystalline CuO and ZnO.

The process described in '072, as noted infra serves as the basis for new catalysts. Indeed, notwithstanding the various catalysts and catalytic processes for ODS, due to issues with hydrocarbon feedstocks, the desired level of desulfurization is not achieved. Also, when molecular oxygen is used as oxidant, it is difficult to control oxidation of the fuel while converting the sulfur components in the fuel oils used. Hence, there is a continuous need for new catalysts useful in ODS.

SUMMARY OF THE INVENTION

The invention relates to a method for gaseous oxidative desulfurization of a sulfur containing hydrocarbon feedstock using a catalyst which comprises from 10 to 50 wt. % CuO, from 5 to less than 20 wt. % ZnO, and from 20 to 70 wt. % $Al_2O_3$, which also contains one or more Group VIB metal oxides, and preferably an acid forming oxide as described supra, which anionically modifies the surface of the catalytic composition, generally by modifying $Al_2O_3$. The total amount of promoters can be present in an amount up to 20 wt. % of the catalyst.

The catalysts, as will be elaborated upon, infra, are prepared by either impregnating a co-precipitated CuZnAl oxide base, or an impregnated $CuZn/Al_2O_3$ oxide base. One or more of Group VIB metal oxides can also be mixed with a wet, co-precipitated CuZnAl oxide base. The catalysts promoted with oxides of VIB metals and with acid forming oxides showed enhanced catalytic performance in ODS processes. When promoted with oxides of both Mo and B, e.g., the catalysts displayed higher total sulfur removal rates, significantly higher ODS selectivity, and excellent reactivity with refractory organosulfur compounds, such as 4,6-DMDBT.

The catalyst described supra is also part of the invention, as are processes for making the catalyst.

BRIEF DESCRIPTION OF THE FIGURES

FIG. 2A and FIG. 2B show the amount of sulfur removed from a model fuel feed with different types of organosulfur compounds, using the catalysts of the invention.

DETAILED DESCRIPTION OF THE INVENTION

Figures 1A, 1B:
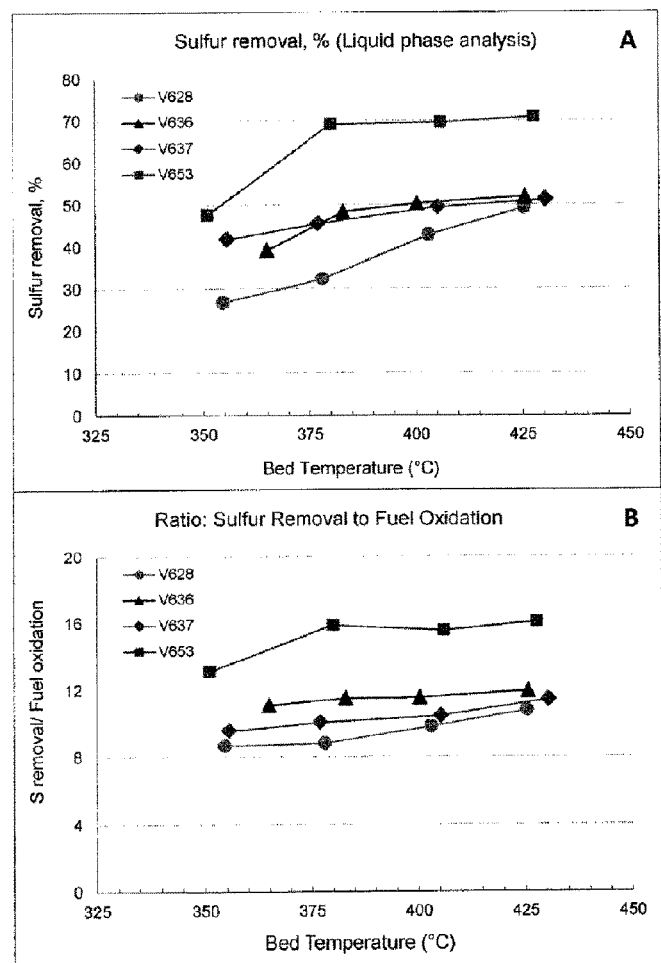
FIG. 1A and FIG. 1B present data for various catalysts made in accordance with the invention, tested to show the role of temperature on total sulfur removal.

The process of the invention will be further described with reference to the disclosure which follows.

Example 1

A CuZnAl composition was prepared via the precipitation method. See, e.g., published U.S. Patent Application 2013/0026072, incorporated by reference, for information on the method.

To elaborate, 0.2 moles of $Cu(NO_3)_2$, 0.01 moles $Zn(NO_3)_2$ and 0.235 moles of $Al(NO_3)_3$ were dissolved in 500 ml of distilled water. This solution will be referred to as "solution A." The pH of solution A was 2.3. "Solution B" was made by dissolving 19.08 g of $Na_2CO_3$ (0.18 moles) and 48 g of NaOH (1.2 moles) together, in 600 ml of distilled water. The pH of solution B was 13.

Solution A was heated to 65° C., and then Solution B was added thereto at a rate of about 5 ml/minute, with constant agitation, until all of Solution B was added. The resulting mixture had a pH of 11.

A precipitate formed and the precipitation slurry was aged for 6 hours at precipitation conditions (65° C., pH 11), and was then cooled to room temperature and filtered with a Buchner funnel. The precipitate was repeatedly washed with distilled water and filtered until pH neutral.

Analysis, using well known techniques, showed that 99% of the Cu, Zn, and Al had precipitated. The precipitate was dried at 110° C. for 12 hours, calcined at 500° C. for 4 hours, and ground to a fine powder.

Two batches of base CuZnAl compositions, labeled as V628 and N543, were prepared. Properties of the compositions of the Example are set forth in Table 1, infra.

Example 2

The composition prepared in Example 1 was then treated to incorporate molybdenum oxide ($MoO_3$), therein, via the well known incipient wetness method.

The calcined, powdered composition of Example 1 was placed in a rotating impregnation drum, and a 0.2 mol/l solution of $(NH_4)_6Mo_7O_{24}$ was fed into the rotating drum. The volume of solution used was 10% more than the calculated water capacity of the CuZnAl composition. The impregnated sample was left in the rotating drum for 20-30 minutes to permit even distribution of the liquid in the powder. The sample was then dried at 110° C., for 12 hours, and calcined at 500° C., for 4 hours. A dark brown solid resulted, and was labeled as V636. Analysis of the calcined product revealed 34-37 wt. % of elemental Cu, 14-14.8 wt. % of elemental Zn, 12-13.5 wt. % of elemental Al, and 3.56 wt. % of elemental Mo. Note that by changing the concentration of $(NH_4)_6Mo_7O_{24}$, the amount of Mo can vary from 2 wt. % to 8 wt. %. It is to be noted that when reference is made to wt. % in these examples, it is by reference to the pure element, not the oxide.

The atomic ratio of Cu:Zn:Al was (2.5-3):1:(2.5-3). The post-calcination composition had a specific surface area of 35-85 m²/g, a pore volume average of 0.15-0.35 cm³/g, and an average pore diameter of 10-20 nm. It contained crystalline CuO, ZnO, and traces of $MoO_3$, and an x-ray amor- The resulting composition was identical to that of Example 1, except it contained 0.9-1 wt. % of B. By varying the concentration of $H_3BO_3$, the amount of B in the final composition, labeled as V637, can range from 0.3-1.5 wt. %.

Example 4

In this example, both $MoO_3$ and $B_2O_3$ were added to the CuZnAl composition of Example 1.

A solution containing $(NH_4)_6Mo_7O_{24}$ (0.22 mol/l) and $H_3BO_3$ (0.5 mol/l) was added to CuZnAl, again as in the prior examples. Drying, calcining, granulation and analysis also took place as per the prior examples.

Four batches of $MoO_3$ and $B_2O_3$ added compositions were prepared, and labeled as V649, V674, V648, and V653 respectively. All properties were as given in Example 1, supra.

TABLE 1

Physico-chemical properties of catalysts used in oxidative desulfurization of model fuel feeds

| Name | Preparation Method | Composition | XRD | $S_{BET}$, m²/g | $V_\Sigma(N_2)$, cm³/g | $D_{BJH}$, nm |
|---|---|---|---|---|---|---|
| V628 | Base Cu—Zn—Al by co-precipitation | $Cu_{2.93}Zn_1Al_{2.8}$ | Highly dispersed spinel CuO, ZnO | 75 | 0.25 | 10.0 |
| N543 | Base Cu—Zn—Al by co-precipitation | $Cu_{3.2}Zn_1Al_{2.6}$ | Highly dispersed spinel CuO, ZnO | | | |
| V636 | Incipient wetness impregnation of base Cu—Zn—Al by $(NH_4)_6Mo_7O_{24}$ solution | 3.56% Mo $Cu_{2.65}Zn_1Al_{3.0}$ | Highly dispersed spinel CuO, ZnO $MoO_3$, minor | 82 | 0.33 | 16.1 |
| V637 | Incipient wetness impregnation of base Cu—Zn—Al by $H_3BO_3$ solution | 1% B $Cu_{2.65}Zn_1Al_{3.0}$ | Highly dispersed spinel CuO, ZnO | 39 | 0.14 | 14.3 |
| V649 | Incipient wetness impregnation of base Cu—Zn—Al by $(NH_4)_6Mo_7O_{24}$ + $H_3BO_3$ solution | 3.13% Mo, 0.84% B $Cu_{2.79}Zn_1Al_{2.8}$ | Highly dispersed spinel CuO, ZnO $MoO_3$, minor | 35 | 0.16 | 18.1 |
| V674 | Incipient wetness impregnation of base Cu—Zn—Al by $(NH_4)_6Mo_7O_{24}$ + $H_3BO_3$ solution | 4.15% Mo, 1.28% B $Cu_{2.79}Zn_1Al_{2.8}$ | Highly dispersed spinel CuO, ZnO $MoO_3$, minor | 38 | 0.18 | 18.6 |
| V648 | Incipient wetness impregnation of base Cu—Zn—Al by $(NH_4)_6Mo_7O_{24}$ + $H_3BO_3$ solution | 3.04% Mo, 0.42% B $Cu_{2.79}Zn_1Al_{2.8}$ | Highly dispersed spinel CuO, ZnO $MoO_3$, minor | 40 | 0.20 | 20.3 |
| V653 | Incipient wetness impregnation of base Cu—Zn—Al by $(NH_4)_6Mo_7O_{24}$ + $H_3BO_3$ solution | 8.25% Mo, 1.59% B $Cu_{2.79}Zn_1Al_{2.8}$ | Highly dispersed spinel CuO, ZnO $MoO_3$, minor | 58 | 0.18 | 13.6 | phous phase. "X ray amorphous phase," as used herein means that, when the product was observed via high resolution transmission electron microscopy ("HRTEM" hereafter), crystalline particles of from 2-10 nm, and more usually, 2-5 nm were observed. The lattice parameters (7.896 Å), were very close to those of spinels.

Properties of the composition of the Example are set forth in Table 1, infra.

Catalytic compositions are granulated by any known method: extrusion, granulation or tabletting by pressing.

Example 3

This example parallels Example 2 except boron (B) was used instead of Mo. The $(NH_4)_6Mo_7O_{24}$ solution was replaced by a 0.5 mol/l $H_3BO_3$ solution.

Example 5

The catalytic compositions prepared in the examples, supra, were tested for their ability to oxidatively desulfurize a model fuel, dibenzothiophene in toluene. An oxygen:sulfur mole ratio of 120, a GHSV of 3,000 hr$^{-1}$, a WHSV of 6 hr$^{-1}$, and temperatures in the range of 250–430° C., were used. The results, presented in FIG. 1 show that the various additives functioned as promoters, enhancing sulfur conversion. Sulfur removal via conversion to $SO_2$ as high as 70 wt. % was secured. Catalyst V653, which is modified by both Mo and B, and with a composition set forth in Table 1 showed superior oxidative desulfurization reactivity. FIGS. 2a and 2b show the impact of organosulfur type on oxidative desulfurization reactivity of catalyst V649, also described in Table 1, supra.

In the examples shown in FIGS. 1 and 2, the temperature ranged from 325-450° C.

While not wishing to be bound to any particular theory, it is noted that the promoters habitually disperse into the catalyst system during ODS reactions. Further, the addition of these promoters changes the redox nature of the catalyst system, which appears to enhance the catalytic performance.

Figure 3:
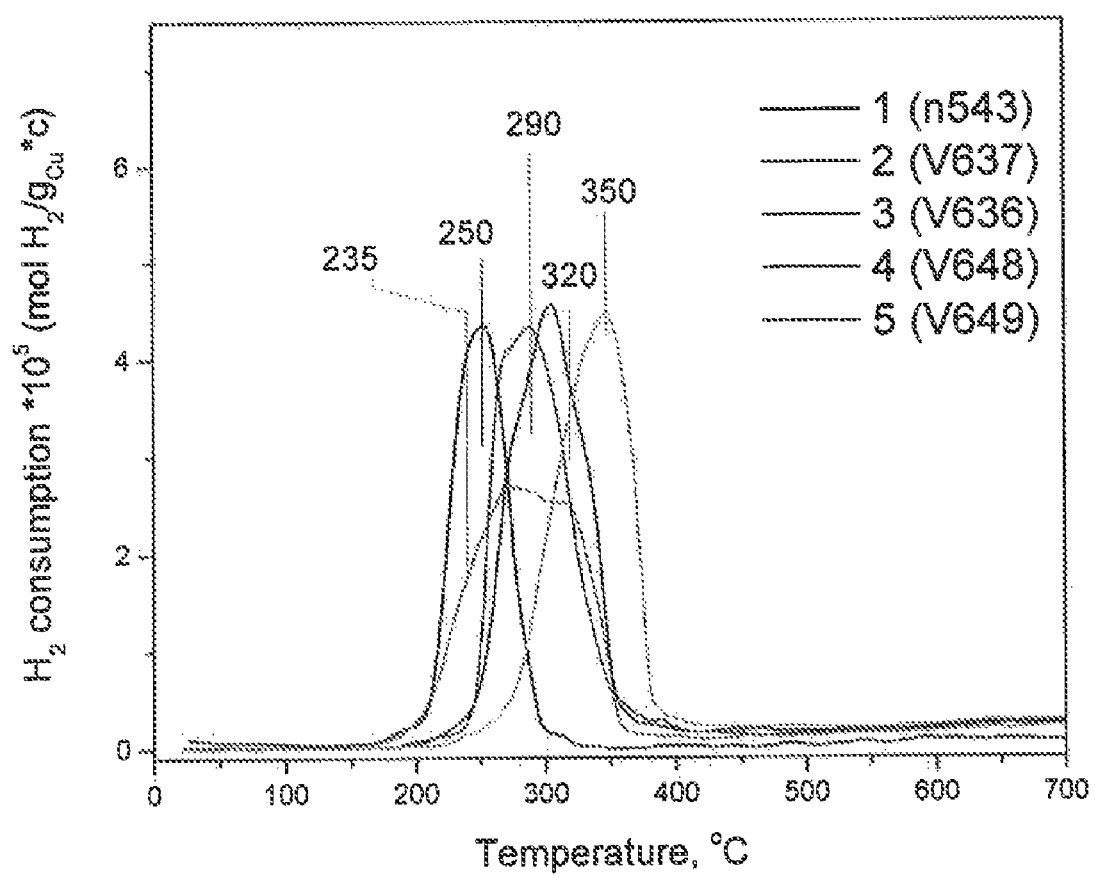
FIG. 3 displays TPR profiles for various catalysts in accordance with the invention.

This can be seen in FIG. 3. Specifically, reduction profiles of CuZnAl catalysts with and without modifiers, referred to supra are shown.

Figure 4:
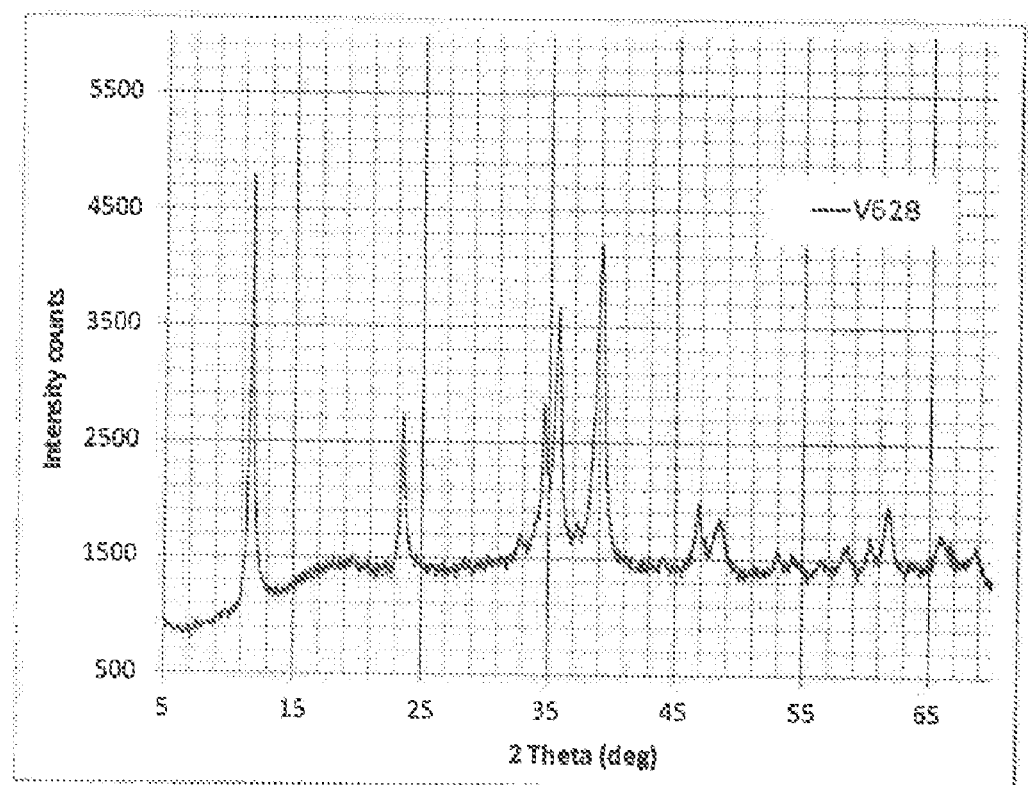
FIG. 4 depicts crystalline structures of a precursor of a catalyst of the invention.

FIG. 4 shows the powder XRD pattern of the dried base CuZnAl catalyst, V628 (after oven drying and before calcination). The XRD pattern shows the presence of a mixed aurichalcite-like phase and a tenornite CuO phase.

Figure 5:
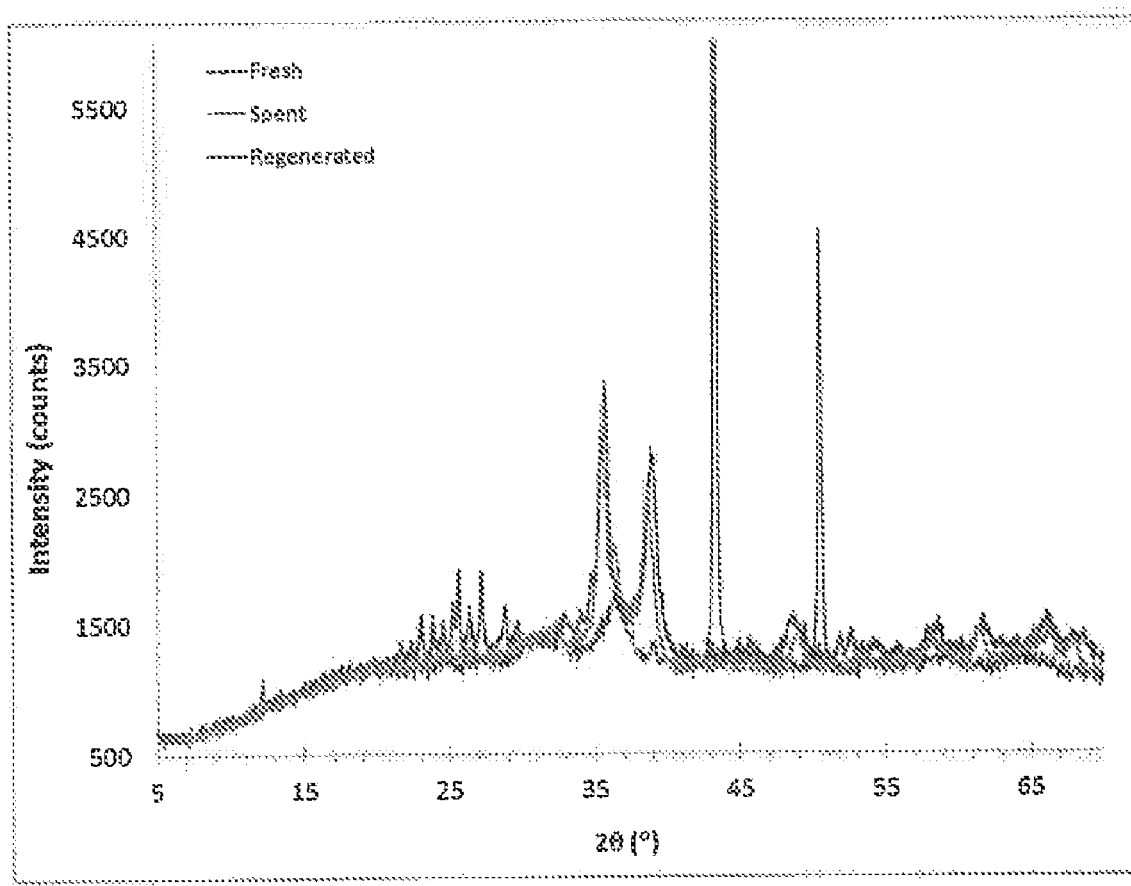
FIG. 5 shows powder X-ray diffraction pattern for fresh, spent, and regenerated catalyst V628, described infra.

FIG. 5 shows the XRD powder pattern of catalyst V649 at three distinctive states of ODS reaction: fresh (after calcination), spent, and regenerated. The XRD pattern of fresh V649 shows three crystalline phases, i.e., CuO, a highly-dispersed solid solution of spinel phase, and a minor molybdenum oxide phase. In FIG. 5, one also observes sharp diffraction peaks of a well crystallized phase metallic copper phase in the XRD pattern of the spent sample. To regenerate the catalyst, it was placed in a flow of $H_2$ containing gas (10% $H_2$), at 350° C. for one hour, followed by purging at room temperature, followed by oxidation in an oxygen containing mixture at 350° C. for one hour, at GHSV 500-3000 hr-1. The XRD pattern of the regenerated catalyst is similar to that of the fresh catalyst except that no crystalline $MoO_3$ phase was identified in the regenerated material. This may indicate that $MoO_3$ existing in the fresh oxide is redispersed during ODS reactivity testing and remains dispersed during regeneration.

The foregoing examples describe features of the invention which include a catalytic composition useful, e.g., in oxidative removal of sulfur from gaseous, sulfur containing hydrocarbons, as well as processes for making the compositions, and their use.

The catalytic compositions comprise oxides of copper, zinc, and aluminum in defined weight percent ranges, and a Group VIB metal oxide promoter. The compositions exhibit an X-ray amorphous oxides phase with crystalline oxides of Zn, Cu, and promoter. Even more preferably, a second promoter, i.e., an acidic oxide of Si, B, or P is added.

As noted, supra, the compositions contain defined amounts of the metallic oxides. The weight percentages permitted by the invention are 5 to less than 20 weight percent zinc oxide, from 10 to 50 weight percent copper oxide, and from 20 to 70 weight percent of aluminum oxide. The promoter is present in an amount up to 20 wt. %.

The aforementioned structure has a lattice parameter corresponding to spinel, according to HRTEM data and the chemical formula $Cu_xZn_{1-x}Al_2O_4$, found from EDX analysis which is in accordance with the standard formula for spinels, i.e., "$MAl_2O_4$," where "M" signifies a metal, herein Zn or Cu, or combination of metals, herein Zn and Cu. Preferably, X ranges from 0.1 to 0.6, more preferably, from 0.2 to 0.5.

The composition of the invention preferably are granular in nature, and may be formed into various embodiments such as a cylinder, a sphere, a trilobe, or a quatrolobe, preferably via processes discussed infra. The granules of the compositions preferably have diameters ranging from 1 mm to 4 mm.

The compositions preferably have specific surface areas ranging from 10 $m^2/g$ to 100 $m^2/g$, more preferably 50 $m^2/g$ to 100 $m^2/g$, with pores ranging from 8 nm to 12 nm, more preferably, 8 nm to 10 nm. In preferred embodiments, the weight percentages are: 20-45 CuO, 10→20 ZnO, and 20-70 $Al_2O_3$, and most preferably 30-45 CuO, 12→20 ZnO, and 20-40 $Al_2O_3$.

The catalytic compositions of the invention are made by preparing an aqueous solution of the nitrates of Cu, Zn, and Al, and then combining this solution with an aqueous alkaline solution which contains NaOH, and/or one or more of $(NH_4)_2CO_3$, $Na_2CO_3$ and $NH_4HCO3$.

These solutions are combined at a temperature which may range from about 50° C. to about 65° C., and at a pH of from about 6.5 to about 14. The resulting hydroxides, carbonates, and/or hydroxycarbonates precipitate and are then filtered, washed, and dried, for at least four hours, at a temperature of at least 100° C., and calcined at an elevated temperature of at least 400° C. Promoter is then added to the composition, preferably via incipient wetness. After this, the resulting dried material is calcined, for about 2-4 hours, at a temperature of at least 450° C., to form the composition described herein.

The precipitate may be aged prior to the filtering and washing, as elaborated in the examples.

It is frequently desirable to form composites of the catalytic composition, and this is preferably done by adding a binder to the compositions prior to calcination. The binder may be, e.g., polyethylene oxide, polyvinyl alcohol, aluminum pseudoboehmite, silica gel, or mixtures thereof. The binder may be added in amounts ranging from about 1 wt. % to about 20 wt. % of the precipitate, preferably from 1-10 wt. % or in the case of hydroxides 3-20 wt. %. The resulting mixture may be extruded through, e.g., a forming die, and then dried, preferably at room temperature, for 24 hours, followed by drying at about 100° C. for 2-4 hours. The extrusion product is then heated slowly, e.g., by increasing temperatures by 2-5° C. every minute until a temperature of 500° C. is reached, followed by calcinations at 500° C. for 2-4 hours.

In practice, the compositions are used by combining them with a sulfur containing hydrocarbon, in gaseous form, together with an oxygen source, such as pure $O_2$, for a time sufficient for at least a portion of the sulfur to be oxidized to, e.g., $SO_2$. The oxygen source is preferably pure oxygen, but may be air, or any other oxygen source. Preferably, the materials recited supra are combined at conditions which include pressure of from 1-30 bars, temperature of from 300° C. to 600° C., with a weight hourly space velocity of from 1-20 $h^{-1}$, gas hourly space velocity of from 1,000-20,000 $h^{-1}$, with an oxygen carbon molar ratio of from 0.01 to 0.1, and a molar ratio of oxygen and sulfur of from 1 to 150. Preferably, the pressure ranges from 1-10 bars, most preferably 1-5 bars, the temperature is preferably from 300-500° C. The gas hourly space velocity is preferably 5,000-15,000 most preferably 5,000 to 10,000 while the preferred molar ration of $O_2$/C ranges from 0.02-0.1, and most preferably from 0.05-0.1, while that of $O_2$/S is from 10-120, and most preferably, from 20-50. Additionally, it is preferred that oxidation take place with the exclusion of hydrogen gas.

The feedstock, e.g., the sulfur containing hydrocarbon, will vary, but preferably is one with a boiling point above 36° C., and even more preferably, above 565° C.

In practice, the catalytic compositions are used in the form of, e.g., fixed beds, ebullated beds, moving beds, or fluidized beds.

Other features of the invention will be clear to the skilled artisan and need not be reiterated here.

The terms and expression which have been employed are used as terms of description and not of limitation, and there is no intention in the use of such terms and expression of excluding any equivalents of the features shown and described or portions thereof, it being recognized that various modifications are possible within the scope of the invention.

We claim:

1. A method of oxidizing sulfur in a sulfur containing hydrocarbon, comprising contacting a gaseous hydrocarbon to a catalytic composition in the presence of an oxygen containing gas at a temperature in the range of from 300-600° C. and a pressure in the range of from 1-30 bars to oxidize sulfur, the catalytic composition comprising copper oxide in an amount ranging from 10 weight percent (wt. %) to 50 wt. %, zinc oxide in an amount ranging from 5 wt. % to less than 20 wt. %, aluminum oxide in an amount ranging from 20 wt. % to 70 wt. %, and at least one promoter selected from the group consisting of a Group VIB metal oxide, wherein said catalytic composition has an X-ray amorphous oxide phase with a formula $Cu_xZn_{1-x}Al_2O_4$ wherein x ranges from 0 to 1, crystalline ZnO and CuO.

2. The method of claim 1, wherein said promoter is Mo or W.

3. The method of claim 1, wherein said promoter further comprises an acidic oxide of Si, B, or P.

4. The method of claim 1, wherein said promoter is present in an amount up to 20 wt. % of said catalyst.

5. The method of claim 1, wherein said hydrocarbon is a gaseous hydrocarbon.

6. The method of claim 1, wherein said oxygen containing gas is pure oxygen.

7. The method of claim 1, comprising oxidizing said hydrocarbon in the absence of hydrogen gas.

8. The method of claim 3, wherein said acidic oxide is $B_2O_3$.

9. A process for making a catalytic composition comprising copper oxide in an amount ranging from 10 weight percent (wt. %) to 50 wt. %, zinc oxide in an amount ranging from 5 wt. % to less than 20 wt. %, aluminum oxide in an amount ranging from 20 wt. % to 70 wt. %, and at least one promoter selected from the group consisting of a Group VIB metal oxide, wherein said catalytic composition has an X-ray amorphous oxide phase with a formula $Cu_xZn_{1-x}Al_2O_4$ wherein x ranges from 0 to 1, crystalline ZnO and CuO, the process, comprising:

(i) combining an aqueous solution containing each of copper nitrate, zinc nitrate, and aluminum nitrate with an alkaline solution containing NaOH and/or at least one of $(NH_4)_2CO_3$, $Na_2CO_3$ and $NH_4HCO_3$, at a temperature of from about 50° C. to about 65° C., and a pH of from about 6.5 to about 14, to form a precipitate containing at least one of (a) a carbonate containing Cu, Zn, and Al, (b) a hydroxide containing Cu, Zn, and Al, and (c) a hydroxycarbonate containing Cu, Zn, and Al;

(ii) aging said precipitate;

(iii) filtering and washing said precipitate;

(iv) drying said precipitate for at least 10 hours, at a temperature of at least 100° C.;

(v) calcining the said dried precipitate for at least 4 hours at a temperature of at least 400° C.;

(vi) adding a solution containing at least one Group VIB compound to said precipitate;

(vii) impregnating said Group VIB compound in said precipitate via incipient wetness, and (viii) calcinating said precipitate for from about 2 to about 4 hours, at a temperature of at least about 450-500° C.

10. The process of claim 9, wherein said aqueous solution further comprises cerium nitrate, and said carbonate, hydroxide, and hydrocarbonate contain Ce.

11. The process of claim 10, further comprising combining the precipitate of (i) with a binder selected from the group consisting of poly-ethylene oxide, polyvinyl alcohol, a sol of aluminum pseudoboehmite, silica gel and mixtures thereof, said binder being added in amount ranging from 1 to 10 weight % of said precipitate, to form an extrudable mixture, extruding said mixture through a die to form an extrudate, drying said extrudate for 24 hours at room temperature to 500° C., at a rate of from 2-5° C./minute, to calcine said extrudate for from 2-4 hours.

12. The process of claim 9, wherein said precipitate comprises hydroxides, said process further comprising combining said precipitate with a binder selected from the group consisting of polyethylene oxide, polyvinyl alcohol, a sol of aluminum pseudoboehmite, silica gel, and mixtures thereof, said binder being added in an amount ranging from 3 to 20 weight percent of said precipitate, to form an extrudable mixture, extruding said mixture through a die to form an extrudate, drying said extrudate for 24 hours at room temperature, followed by drying at 100° C. for from 2-4 hours, and raising temperature to 500° C., at a rate of from 2-5° C./minute, to calcine said extrudate for from 2-4 hours.

13. The process of claim 9, comprising adding a solution containing a water soluble Mo(VI) or W(VI) compound to provide an $MoO_3$ or $WO_3$ phase upon calcination.

14. The process of claim 9, comprising further adding a solution containing a water soluble compound of B(III) to provide $B_2O_3$ upon calcination.

* * * * *